United States Patent [19]  [11] 4,267,384
Smith  [45] May 12, 1981

[54] RUTHENIUM CATALYZED PROCESS FOR ACETALDEHYDE AND ETHANOL

[75] Inventor: David W. Smith, Cincinnati, Ohio

[73] Assignee: National Distillers and Chemical Corp., New York, N.Y.

[21] Appl. No.: 142,286

[22] Filed: Apr. 21, 1980

[51] Int. Cl.³ .............. C07C 27/00; C07C 31/08; C07C 47/06
[52] U.S. Cl. ............................. 568/462; 568/881
[58] Field of Search ..................... 568/462, 881

[56] References Cited

U.S. PATENT DOCUMENTS

| | | | |
|---|---|---|---|
| 1,311,824 | 7/1919 | Lichtenhahn | 568/881 |
| 2,451,333 | 10/1948 | Gresham et al. | 568/865 |
| 2,614,107 | 10/1952 | Wender et al. | 568/881 |
| 3,102,150 | 8/1963 | Hunter et al. | 568/881 |
| 3,285,948 | 11/1966 | Butter | 568/902 |
| 3,454,644 | 7/1969 | Dewhirst | 568/881 |
| 3,925,490 | 12/1975 | Reich et al. | 568/881 |
| 4,133,966 | 1/1979 | Pretzer et al. | 568/902 |
| 4,200,765 | 4/1980 | Goetz | 568/462 |

FOREIGN PATENT DOCUMENTS 175238  11/1922  United Kingdom ............. 568/881

Primary Examiner—Joseph E. Evans
Attorney, Agent, or Firm—Kenneth D. Tremain

[57] ABSTRACT

Acetaldehyde and ethanol are produced by the reaction of formaldehyde, carbon monoxide and hydrogen using a halogen-containing ruthenium catalyst.

22 Claims, No Drawings

RUTHENIUM CATALYZED PROCESS FOR ACETALDEHYDE AND ETHANOL

This invention is concerned with processes for the preparation of acetaldehyde, and conversion thereof to ethanol, by reaction of formaldehyde, carbon monoxide and hydrogen in the presence of a ruthenium catalyst.

Acetaldehyde is a very valuable commercial chemical with a wide variety of uses particularly as an intermediate for production of commercial chemicals. Ethyl alcohol is also an important, valuable commercial chemical useful for a wide variety of purposes including as a chemical intermediate, as a solvent, and perhaps more importantly as a component of gasohol.

The reaction of formaldehyde with carbon monoxide and hydrogen is a known reaction and yields, inter alia, ethylene glycol, methanol, and higher polyhydroxy compounds. For example, U.S. Pat. No. 2,451,333 describes the reaction of formaldehyde, carbon monoxide and hydrogen over a cobalt catalyst to produce mixtures of polyhydroxy compounds which include ethylene glycol, glycerol, and higher polyols. Various metal catalysts are also disclosed including nickel, manganese, iron, chromium, copper, platinum, molybdenum, palladium, zinc, cadmium, ruthenium and compounds thereof.

U.S. Pat. No. 3,920,753 describes the production of glycol aldehyde by reaction of formaldehyde with carbon monoxide and hydrogen in the presence of a cobalt catalyst under controlled reaction conditions, but with comparatively low yields.

Polyols are also produced by reaction of carbon monoxide and hydrogen over various metal catalysts. U.S. Pat. No. 3,833,634 describes this reaction catalyzed by rhodium to produce ethylene glycol, propylene glycol, glycerol, methanol, ethanol, methyl acetate, etc. Rhodium catalysts are also employed in the production of oxygenated derivatives of alkenes, alkadienes and alkenoic acid ester by reaction with carbon monoxide and hydrogen, as described, for example, in U.S. Pat. Nos. 3,081,357; 3,527,809; 3,544,635; 3,577,219; and 3,917,661.

The prior art processes for production of ethylene glycol have characteristically provided mixtures of products, the principal co-products being propylene glycol and glycerine, along with the lower alcohols, methyl and ethyl alcohol.

In commonly assigned, copending patent application Ser. No. 884,877, filed Mar. 9, 1978, now U.S. Pat. No. 4,200,765, there is described the process of selectively producing ethylene glycol to the exclusion of other polyol compounds by reaction of formaldehyde, carbon monoxide and hydrogen in the presence of a rhodium catalyst. Also produced along with ethylene glycol is methanol as the monohydroxy product. Further, when the reaction is conducted in two stages, the first stage leads to production of glycol aldehyde, along with methanol, and in the second phase, the glycol aldehyde is converted to ethylene glycol.

It has now been found that the reaction of formaldehyde, carbon monoxide and hydrogen over certain selected ruthenium catalysts involves a two-stage reaction, with the first stage principally yielding acetaldehyde and methanol, and the second stage principally yielding ethanol. Thus, this reaction involves homologation of formaldehyde to acetaldehyde in the first stage in substantial yield from which substantial quantity of ethanol can be produced in the second stage, if desired.

Thus, in the preferred forms of the invention, the present process provides acetaldehyde in excellent yields from formaldehyde, carbon monoxide and hydrogen, and provides ethanol in substantial yield as a second stage product, or, if desired, as the product of the overall process without separate stage reactions.

The very desirable results obtained in accordance with the present process renders the process particularly amenable to commercial production of acetaldehyde and ethanol, not only from the viewpoint of the substantial yields of the products, but also the ease of recovery from the co-produced methanol, e.g., by fractional distillation. The ease of recovery is extremely important since it permits separation of the products from the reaction mixture even in those process runs where methanol may be produced as the major product. Thus, for example, even where acetaldehyde is present in amounts corresponding to about 10 mole-percent, and even less, of the reaction product mixture, the ease of separation will permit recovery of the aldehyde.

Acetaldehyde is also produced in a high order of purity. Usually, the first stage reaction mixture can be used as such in the second stage reaction to produce ethanol by reduction of acetaldehyde.

The process of the present invention is accomplished by contacting formaldehyde, carbon monoxide and hydrogen, preferably in a suitable solvent, in the presence of certain ruthenium-containing catalysts at elevated temperature and superatmospheric pressure. The major product of the two-stage reaction is ethanol, with the major by-product being methanol. The manner of contact is not critical since any of the various procedures normally employed in this type of reaction can be used as long as efficient gas-liquid contact is provided. Thus, the process may be carried out by contacting a solution of formaldehyde together with the ruthenium catalyst with a mixture of carbon monoxide and hydrogen at the selected conditions. Alternatively, the solution of formaldehyde may be passed over the catalyst in a trickle phase under a mixture of carbon monoxide and hydrogen at the selected conditions of temperature and pressure.

In view of the two-stage nature of the present process to produce ethanol, the implementation can take several forms. The reaction can be accomplished by allowing both stages to proceed consecutively at suitable temperature and pressure, or alternatively, the reaction can be stopped at the end of the first phase where the product is acetaldehyde and the second phase can be carried out under any applicable reduction process which will result in conversion of the aldehyde group of acetaldehyde to the primary alcohol group of ethanol.

A wide variety of reduction processes can be employed for the second phase reaction including the well-known chemical reducing agents employed in reducing aldehydes to primary alcohols. For commercial processes, however, where possible, catalytic reductions employing hydrogen are usually preferred since they are more practical and efficient especially with catalysts which can be regenerated. In the present process, catalytic hydrogenation is preferred for these same reasons, especially with catalysts which can be regenerated. Any hydrogenation catalyst effective for carbonyl reduction can be employed.

Thus, typical hydrogenation catalysts include, for example, Raney Nickel, cobalt, copper chromite, rhodium, palladium, platinum, and similar such metal catalysts, which can be used conveniently on supports such as charcoal, silica, alumina, kieselguhr and the like. The conditions of catalytic hydrogenation are well-known and, in general, the reaction can be conducted at temperatures ranging from about 30° to about 150° C., usually at pressures of from about 100 to about 5000 psig. The use of higher temperatures and pressures, though operable, provides no special advantage and usually requires special equipment which economically is disadvantageous and therefore not preferred.

Particularly preferred catalysts are those which characteristically require short reaction times, e.g., palladium and nickel, which is most desirable for commercial processes for economic reasons.

The active catalyst species of the catalyst system for the present process has not been fully identified but it is assumed to be comprised of ruthenium in complex combination with carbon monoxide together with a halide ligand. It is sufficient that the catalyst system initially comprise a source of ruthenium and a source of halide and the active catalyst species then forms on initiation of the process, e.g., the complex ruthenium carbonyl will form on addition of the reactants, i.e., carbon monoxide and hydrogen. Alternatively, the ruthenium source can be a preformed complex carbonyl. Further, the source of both ruthenium, or ruthenium carbonyl complex, and halide can be the same compound, e.g., ruthenium carbonyl halides which are commercially available. The catalyst systems can be formed with ruthenium carbonyl halides or alternatively by the combination of ruthenium carbonyl or hydrocarbonyl complexes with a separate source of halide. The catalyst system can be employed as such or deposited or affixed to a solid support such as molecular sieve zeolites, alumina, silica, ion exchange resin or a polymeric ligand. The preferred halides are chloride and bromide, especially chloride. The ruthenium halocarbonyl catalysts may be represented by the formula $Ru_a(CO)_bX_c$ wherein a, b and c are integers and X is halide, preferably chloride. Such catalysts may be prepared by reaction of ruthenium halides with carbon monoxide or by reaction of ruthenium carbonyl complexes with halogen-containing compounds. Alternatively, ruthenium carbonyl halides are available commercially, (e.g., from Matthey-Bishop, Malverne, PA).

The catalysts of this invention may contain other ligands in addition to halide ligand which must be present for the present process. As described in U.S. Pat. No. 3,833,634, suitable ligands are compounds which contain at least one nitrogen and/or at least one oxygen atom, said atoms having a pair of electrons available for formation of coordinate bonds with ruthenium. Illustrative organic ligands include various piperazines, dipyridyls, N-substituted diamines, aminopyridines, glycolic acid, alkoxy-substituted acetic acids; tetrahydrafuran, dioxane, 1,2-dimethoxybenzene, alkyl ethers of alkylene glycols, alkanolamines, iminodiacetic acid, nitrilotriacetic acid, ethylenediaminetetraacetic acid, and the like. In U.S. Pat. No. 3,527,809 are described phosphorus-containing ligands such as trialkyl, triaryl and tricycloalkyl phosphites and triarylphosphines, as well as the analogous antimony and arsenic compounds.

The phosphine-containing catalysts usually provide a higher ratio of alcohol to aldehyde than do the same catalysts without phosphine ligands.

The phosphine-containing catalysts can be prepared by the methods described in the aforesaid U.S. Pat. No. 3,527,809 employing suitable ligands exemplified as follows:

Trimethylphosphine
Triethylphosphine
Tri-n-butylphosphine
Triamylphosphines
Trihexylphosphines
Tripropylphospine
Trinonylphosphines
Tridecylphosphines
Triethylhexylphosphine
Di-n-butyl octadecylphosphine
Dimethyl-ethylphosphine
Diamylethylphosphine
Tris(dimethylphenyl)phosphine
Ethyl-bis(beta-phenylethyl)phosphine
Tricyclopentylphosphine
Tricyclohexylphosphine
Dimethyl-cyclopentylphosphine
Tri-octylphosphine
Dicyclohexylmethylphosphine
Phenyldiethylphosphine
Dicyclohexylphenylphosphine
Diphenyl-methylphosphine
Diphenyl-butylphosphine
Diphenyl-benzylphosphine
Trilaurylphosphine
Triphenylphosphine The activity of the ruthenium catalyst systems of this invention is increased by the addition of certain metal salts, particularly halide salts. In present experience, the most preferred are alkali metal halides, especially lithium chloride and lithium bromide. Various such salts, on addition to the catalyst system, increase the total production of methanol and $C_2$-oxygenated products ethanol and acetaldehyde.

For most purposes, the amount of halide employed can be varied considerably, with molar ratios of at least about 0.1 mole per mole of ruthenium being operable.

In lieu of addition of alkali metal salts, preferably halides, the salts can be used with the selected catalyst to produce ruthenium halocarbonyl anions which, for the purpose of this disclosure, are represented by the general formula $M_aRu_bX_c(CO)_d$ wherein a, b, c and d are integers, e.g. $NaRuBr_3(CO)_3$ and $NaRuCl_3(CO)_3$. Such compounds can be preformed and then added to the reaction in solent as the catalyst system.

The hydrohalic acids HCl and HBr also promote the activity of the ruthenium halocarbonyls and non-halogen containing ruthenium compounds of the present new process. Large excesses of hydrogen halides are of no advantage and are usually avoided since they may tend to decrease catalyst activity.

In addition, the catalysts for this invention can also be formed by addition of halide, e.g., as alkali metal halide or hydrogen halide, to a suitable ruthenium compound in the selected solvent or in the reaction mixture, if preferred. For example, ruthenium carbonyl in combination with hydrogen halide in reaction solvents provides essentially the same results as preformed catalysts, e.g., $[Ru(CO)_2Cl]_2$. It is noted that, in the absence of hydrogen halide, e.g., HCl or HBr, the ruthenium catalyst, such as ruthenium carbonyl, form methanol as the principal product with little, if any, ethanol or acetaldehyde. The amounts of halide added to the catalyst need not be stoichiometric since even small amounts will result in the production of some ethanol. For most purposes, however, it is preferred to employ at least an equimolar amount of halide which can be added as aqueous solution or solution in organic solvents, such as the lower alkanols. When employed, the metal halides are conveniently alkali metal halides such as lithium fluoride, potassium bromide and sodium chloride.

The determination of suitability of starting ruthenium compounds to be used for the formation of the halide-containing catalyst can be accomplished by a simple test procedure which involves running small scale reactions with the selected ruthenium compound, alkali metal halide or hydrogen halide and reactants $H_2CO$, CO and $H_2$ in solvent. At the completion of the miniature reactions, gas-liquid chromatographic analyses of the reaction mixture will identify the products and, of course, will identify those ruthenium compounds which are suitable, through in situ treatment, for production of ethanol and/or acetaldehyde. Using this test procedure, suitable starting ruthenium compounds are easily identified.

Catalysts formed in situ, however, appear to produce comparatively large quantities of methanol and other products along with less acetaldehyde and ethanol. The preformed catalysts, however, only product relatively low amounts of by-products and substantial yields of acetaldehyde and ethanol. Thus, the preformed catalysts are preferred for production of acetaldehyde and ethanol.

The catalyst can be employed in soluble form or in suspension in the reaction medium, or alternatively deposited on porous supports.

When acetaldehyde is the desired product, of course, only the first stage reaction need be carried out. The product can be separated from the co-produced methanol, any ethanol formed and reaction solvent, if necessary, by fractional distillation.

As should be apparent, the ruthenium catalyst employed in the first stage reaction can also serve as the hydrogenation catalyst for the second stage reaction to produce ethanol. Thus, if the first phase reaction is allowed to continue, eventually the hydrogenation reaction will yield ethanol. In general, the ruthenium catalyst of the first stage reaction is an effective catalyst for the second stage hydrogenation, but other hydrogenation catalysts can be used in lieu of the ruthenium catalyst.

It is possible to effect th reduction step over metal catalysts such as palladium and nickel, or copper chromite and it is usually preferred to effect the second stage reaction in a separate reactor. Thus, the first stage reaction can be conducted in a first reactor under selected conditions of temperature and pressure, and after completion the first stage product, with or without isolation from the reaction mixture, can then be transferred to a second reactor under selected conditions of temperature and pressure to effect the hydrogenation reaction.

Alternatively, the two-stage reaction can be conducted in one reactor with provision for controlling the reaction parameters. At the time of the hydrogenation stage, the selected hydrogenation catalyst can be added and the hydrogenation reaction can then proceed. In this latter modification, the hydrogenation catalyst can be added to the first phase reaction mixture with or without the first phase ruthenium catalyst being present. Generally, it is preferred to remove the ruthenium catalyst, particularly if this can be done conveniently so that competitive catalysts will not impede the hydrogenation reaction, and, more importantly, to permit more accurate control over the reaction.

There of course is no criticality about stopping the reaction exactly at the termination of the first stage, or holding the second stage reaction until all acetaldehyde is reduced to ethanol. The reaction can be stopped at any convenient point which will be dictated by the product desired, along with other considerations. Thus, after substantially maximum yield of acetaldehyde is obtained, usually within about 2 hours, the reaction can be stopped and the aldehyde recovered. However, the reaction mixture will undoubtedly contain quantities of ethanol formed through the second stage reaction. The products, however, are easily separable and are almost equally commercially important. Obviously, where ethanol is desired, the reaction can be allowed to proceed, within economic considerations, until reasonably complete to obtain ethanol as the major product, and of course acetaldehyde the minor product.

Usually, lower reaction temperatures seem to favor acetaldehyde production, even where long reaction times are used, whereas higher temperatures favor ethanol production. It has been observed that at about 120° C., acetaldehyde is the major product, even after several hours, e.g., up to 4-5 hours, whereas at 175° C. the major product is ethanol.

The present invention, therefore, provides a simplified process for selective production of acetaldehyde. In addition, this invention affords a simplified process for obtaining ethanol by either allowing the initial process for aldehyde production to continue so that hydrogenation yields ethanol or, alternatively, the aldehyde product of the first stage reaction is reduced employing art-recognized reduction processes to ethyl alcohol. In the latter process, the acetaldehyde product of the first stage reaction can be used in the form of the reaction mixture, or the product can be isolated, as by fractionation, and used in purified form.

The amount of catalyst employed in the first stage reaction does not seem to be critical and can vary considerably. At least a catalytically effective amount of catalyst should be used, of course. In general, an amount of catalyst which is effective to provide a reasonable reaction rate is sufficient. As little as 0.001 gram atoms of ruthenium per liter of reaction medium can suffice while amounts in excess of 0.1 grams atoms do not appear to materially affect the rate of reaction. For most purposes, the effective preferred amount of catalyst is in the range of from about 0.002 to about 0.05 gram atoms per liter.

The reaction conditions are not overly critical in that wide ranges of elevated temperature and superatomospheric pressures are operable. The practical limitations of production equipment will dictate to a great extent the selection of temperatures and pressure at which the reaction is to be effected. Thus, using available production systems, the selected elevated temperature should be at least about 75° C. and can range up to about 250° C. and even higher. For most purposes, the preferred operating temperature ranges from about 100° to about 175° C. The superatmospheric pressure should be at least about 10 atmospheres and can range up to almost any pressure attainable with production apparatus. Since extremely high pressure apparatus is quite expensive, pressures to about 700 atmospheres are suggested. Most desirably, the pressure should be in the range of from about 150 to about 600 atmospheres, particularly when employing the aforesaid preferred temperature range.

The reaction is preferably carried out in a solvent which will dissolve polar materials and which preferably is aprotic. The preferred solvents are N-substituted amides in which each hydrogen of the amido nitrogen is substituted by a hydrocarbon group, e.g., 1-methyl-pyrolidin-2-one, N,N-dimethylacetamide, N,N-diethylacetamide, N-methylpiperidone, 1,5-dimethylpyrrolidin-2-one, 1-benzyl-pyrrolidin-2-one, N,N-dimethylpropionamide, hexamethylphosphoric triamide and similar such liquid amides. The amides are preferred solvents since their use results in the highest yields of product in present experience. Other solvents, usually aprotic, can be used but the yields are substantially less than obtained with the preferred amide solvents. Such solvents include, for example, liquid alkyl-substituted ureas, e.g., 1,1,3,3-tetramethyl urea, cyclic ethers such as tetrahydrofuran, dioxane and tetrahydropyran; ethers such as diethyl ether, 1,2-dimethoxybenzene; alkyl ethers of alkylene glycols and polyalkylene glycols, e.g., methyl ethers of ethylene glycol, propylene glycol and di-, tri- and tetraethylene glycols; ketones such as acetone, methyl isobutyl ketone, and cyclohexanone; esters, such as ehtyl acetate, ethyl propionate and methyl laurate; lactones of organic carboxylic acids such as butyrolactone and valerolactone, organic acids such as acetic acid, propionic acid and caproic acid; and alkanols, such as methanol, ethanol, propanol, 2-ethylhexanol and the like; and mixtures thereof. The selected solvent should preferably be liquid under the reaction conditions.

The preferred solvents are aprotic organic amides. The contemplated amides include cyclic amides, i.e., in which the amido group is part of a ring structure such as in pyrrolidinones and piperidones; acylated cyclic amines, such as N-acyl piperidines, pyrroles, pyrrolidines, piperazines, morpholines, and the like, preferably in which the acyl group is derived from a lower alkanoic acid, e.g., acetic acid; as well as acyclic amides, i.e., wherein the amido group is not part of a ring structure as in acetamides, formamides, propionamides, caproamides and the like. The most preferred of the amides are those in which the amido hydrogen atoms are fully replaced by hydrocarbon groups preferably containing not more than 8 carbon atoms. Exemplary hydrocarbon groups are alkyl, preferably lower alkyl such as methyl, ethyl and butyl; aralky, such as benzyl and phenethyl; cycloalkyl, such as cyclopentyl and cyclohexyl; and alkenyl, such as allyl and pentenyl. The preferred amido nitrogen substituents are lower alkyl, especially methyl, ethyl and propyl groups and aralkyl groups, especially benzyl. The most preferred amide solvents include 1-methylpyrrolidin-2-one, 1-ethylpyrrolidin-2-one, and 1-benzylpyrrolidin-2-one. Of course, mixtures of solvents can be used, e.g., amide solvent with other solvents.

Water is not critical to the reaction and can be present without serious adverse effect. It tends to react with carbon monoxide to form $CO_2$ and hydrogen (water gas shift). Water can be excluded since it can reduce the selectively of conversion of carbon monoxide, or the water-gas shift can be used advantageously to generate hydrogen.

The reaction pressures represent the total pressure of the gases contained in the reactor, i.e., carbon monoxide and $H_2$, if present, any inert diluent gas such as nitrogen. As in any gaseous system, the total pressure is the sum of partial pressures of component gases. In the present reaction, the molar ratio of hydrogen to carbon monoxide can range from about 1/10 to about 10/1, with the preferred ratio, from about 1/5 to about 5/1, and the reaction pressure can be achieved by adjusting the pressure of these gases in the reactor.

Where the second phase reaction is carried out in a separate reactor whether over the originally present ruthenium catalyst or a different metal hydrogenation catalyst, the reaction is normally conducted under hydrogen gas without diluent gas, as is usual in catalyzed hydrogenation reactions.

The source of formaldehyde for the present process can be any of those commonly used in this technology including paraformaldehyde, methylal, formalin solutions, and polyoxymethylenes. Of these, paraformaldehyde is preferred since best yields are attained therewith. Solutions of formaldehyde in solvents, advantageously the reaction solvent, can be used, e.g., aqueous solutions of formaldehyde in reaction solvent, such as N-methyl pyrrolidin-2-one. The use of methylal may be attended by a reduction in yield of products. If trioxane is employed, because of its stability, a hydrolyzing agent should be employed to release formaldehyde.

As with any process of this kind, the present process can be conducted in batch, semi-continuous, and continuous operation. The reactor should be constructed of materials which will withstand the temperatures and pressures required, and the internal surfaces of the reactor are substantially inert. The usual controls can be provided to permit control of the reaction such as heat-exchangers and the like. The reaction should be provided with adequate means for gas-liquid contact such as by vibration, shaking, stirring, oscillation, trickle column operation and like methods. Catalyst as well as reactants may be introduced into the first stage or the second stage reactor at any time during the process for replenishment. Recovered catalyst, solvent and unreacted starting materials may be recycled.

The relative yields of ethyl alcohol, acetaldehyde and methanol are not overly critical since the product mixture can be readily separated into the components by known techniques, especially by fractional distillation, regardless of the proportions contained in the mixture. Therefore, even where the desired product is 10–20% of the reaction mixture, it can be readily separated from the mixture, especially under continuous processing. Of course, the preferred processes yield mixtures in which acetaldehyde and ethanol predominate as the reaction product and methanol, as a by-product, is minimal.

The effect of temperature variation in the preferred temperature range is not as pronounced, with higher formaldehyde conversion being obtained in the 100°–175° C. range, particularly during the first stage reaction.

The process conditions for the separate first stage reaction are essentially the same as employed in the first stage of the combined two-stage reaction. Thus, the reaction is carried out at a temperature as low as about 75° C. to obtain a reasonable reaction rate although somewhat lower temperatures can be employed with slower reaction rates being realized. For reaction times of about one hour, and even less, the temperature should be in the range of from about 100° C. to about 175° C., preferably from about 120° to about 160° C. The total pressure of gas used is generally maintained at from about 10 up to about 700 atmospheres, with from about 150 to about 400 atmospheres being preferred. Of course, higher pressures and higher temperatures can be used but with no appreciable advantage and, since they require the use of special high pressure equipment, they are usually avoided.

The reaction conditions employed in the second stage reaction, i.e., the hydrogenation, can be any of the standard reaction temperatures and pressures employed for such reactions since neither temperature nor pressure are critical for this reaction. Preferably, the hydrogenation is conducted at a temperature of at least about 100° C. in order to effect a reasonable reaction rate. Of course, lower temperatures can be used if longer reaction times can be tolerated. The pressure of hydrogen gas is not excessively critical as long as sufficient gas is available for the hydrogenation. For convenience, the pressure will range from about 500 psi to as much as 5000 psi, although even higher pressures can be employed.

When the catalyst selected for the hydrogenation step is other than ruthenium, it is preferred to remove the ruthenium catalyst from the first stage reaction mixture. This preference is primarily predicated on the desirability of avoiding concomitant catalytic effects which may tend to reduce the yield of ethanol.

The following examples further illustrate the invention. The equipment, synthetic procedure and analyses employed are as follows:

I. Equipment

A. Reactors

Reactions were carried out in Parr 71 ml reactors constructed of 310SS having one Type A ¼" coned socket (Cat. #4740, Parr Instrument Co., Moline, IL). Glass liners with open tops were employed. Reactor seal was a modified Bridgeman type, incorporating a special two piece gasket (Cat. #61HD), comprising silver (exposed to process) with a nickel back-up ring. This gasket arrangement was necessitated due to attack by carbon monoxide of the originally supplied one-piece nickel gasket.

The reactors were capped with 316SS Whitey severe service valves with high temperature Grafoil packing (Cat. #SS3NBS4-GTA-9K-3N, Whitey Co., Oakland, CA). The valves were coupled to the reactors with 316SS Sno-Trik male high pressure to Swagelok adapters (Cat. #SS-44M-A-400, Sno Trik Co., Solon, OH), and Swagelok port connectors (Cat. #SS-401-PC, Crawford Fitting Co., Cleveland, OH).

B. Agitation and Heating

The arm of a Burrell wrist action shaker was projected into an oven comprising an insulated box and electrical strip-heaters. Reactors were clamped to the shaker arm. Oven temperature was measured by a thermocouple which connected to a controller (on-off type). A timer was used to control reaction time by interrupting power to the temperature controller at the desired time. The temperature controller was used to activate a relay coil. A Variac was used to regulate the voltage going to the heater from the relay.

In cases where more vigorous agitation was required, the reactors (without glass liners) were bolted to a paint shaker by means of a special bracket which prevented whip action of the valve which could cause the port connector to sever.

C. Gas Compression and Delivery

Custom carbon monoxide-hydrogen mixtures (Union Carbide Corp., Linde Division, South Plainfield, NJ) were piped into an air driven, double-ended compressor (Cat. #46-14035, American Instrument Co., Silver Spring, MD), thence the reactor through a line containing shut-off and vent valves and a pressure gauge.

II. Synthesis Procedure

Reactor charging and sealing generally were carried out in a nitrogen atmosphere (glove bag). Catalyst (about 0.02 gm) paraformaldehyde (usually 0.5 gm) or other substrate and additives were weighed into a glass liner which then was placed in the reactor. Solvent (5 ml) and liquid additives (usually air free) were added by syringe or pipette. The reactor was sealed and capped with a valve.

The reactor was connected to the compressor discharge system and purged with the desired gas by pressurizing, then venting several times. Then gas was compressed into the reactor to the desired pressure (2000–4500 psig) as indicated on the system gauge. After gas feed-line venting, the reactor was disconnected, and the valve plugged to prevent leakage through the seal.

After heating (80°–250° C.) and shaking the reactor for the desired time, it was cooled then vented through a wet test meter with a gas sample being taken. The liquid contents were discharged, and the reactor and liner rinsed with solvent. The combined liquid for analysis was 15 gm.

III. GLC Analysis Procedure

GLC analysis were performed on a Varian-Aerograph Series 1400 chromatograph equipped with hydrogen flame detector. A 6'×⅛" O.D. 316SS column packed with 80–100 mesh Chromosorb 102 was utilized. The operating temperatures were 150° C. column, 250° C. injector, 250° C. detector. The gas flow rates were 30 ml/min. He, 30 ml/min. H$_2$, 300 ml/min., air.

EXAMPLE 1

Employing the procedure and apparatus already described, the Parr reactor was charged with 0.025 g. [Ru(CO)$_3$Cl$_2$]$_2$, 0.5 g. paraformaldehyde, and 5 ml. N-methylpyrrolidin-2-one at 4500 psig initial pressure at different temperatures and for varied time and molar ratios of H$_2$:CO with the results given in TABLE I.

In the last recorded run, the catalyst concentration was reduced to 0.011 g.

TABLE I

| Reaction | | H$_2$:CO | Products Yields, % | | | |
|---|---|---|---|---|---|---|
| Temp. °C. | hrs. | Molar Ratio | CH$_3$OH | CH$_3$CHO | C$_2$H$_5$OH | C$_3$H$_7$OH |
| 80 | 6 | 1:1 | 3.6 | 5.5 | tr. | 0 |
| 120 | 2 | 1.5:1 | 9.3 | 25.1 | 0.3 | 0 |
| 150 | 2 | 1:1 | 14.1 | 21.6 | 9.9 | 0.4 |
| 150 | 2 | 1.5:1 | 17.6 | 14.3 | 20.9 | 0.8 |
| 175 | 2 | 1.5:1 | 26.3 | 13.8 | 19.4 | — |
| 175 | 2 | 1:3 | 23.8 | 16.9 | 6.2 | — |

TABLE I-continued

| Reaction | | H$_2$:CO | Products Yields, % | | | |
|---|---|---|---|---|---|---|
| Temp. °C. | hrs. | Molar Ratio | CH$_3$OH | CH$_3$CHO | C$_2$H$_5$OH | C$_3$H$_7$OH |
| 175 | 2 | 1:1 | 16.5 | 19.9 | 2.4 | 0.3 |

EXAMPLE 2

The procedure of EXAMPLE 1 was repeated.

The charge to the reactor was 0.025 g. (0.048 mmole) catalyst of EXAMPLE 1; 0.5 g. paraformaldehyde; and 1:1 H$_2$:CO at 4500 psig initial pressure for each of four runs.

The results are given in TABLE II in which runs 1 and 3 contained no triphenylphosphine while runs 2 and 4 contained 0.0209 g (0.08 mmole) triphenylphosphine.

TABLE II

| Run | Temp. °C. | Time, hrs. | Product Yields, % | | | | |
|---|---|---|---|---|---|---|---|
| | | | CH$_3$OH | CH$_3$CHO | C$_2$H$_5$OH | C$_3$H$_7$OH | CH$_2$(OCH$_3$)$_2$ |
| 1 | 120 | 1 | 5.8 | 13.4 | 0.1 | tr. | tr. |
| 2 | 120 | 1 | 7.7 | 8.6 | 0.8 | — | .8 |
| 3 | 150 | 2 | 14.1 | 21.6 | 9.9 | .4 | 1.9 |
| 4 | 150 | 2 | 34.1 | 14.5 | 16.9 | .2 | 5.8 |

EXAMPLE 3

The reactor was charged with 0.07 g. Ru$_3$(CO)$_{12}$; 0.5 g. paraformaldehyde; 5 ml. N-methylpyrrolidone and 1.5:1 H$_2$:CO at 4500 psig initial pressure and then heated at 120° C. for five hours.

After completion, the reaction mixture was analyzed to find that the major product was methanol, with no ethanol or acetaldehyde detected.

This procedure was repeated with RuCl$_3$H$_2$O at 120° C. and 175° C. At the former temperature, the major product was methanol with little or no detectable acetaldehyde or ethanol but at the latter, acetaldehyde (ca. 6%) and ethanol (ca. 2%) were obtained.

EXAMPLE 4

The procedure of EXAMPLE 1 was repeated with the following charge:
0.0199 gm Ru$_3$(CO)$_{12}$
1 ml HBr/NMP solution containing 0.1 mmole HBr per ml
4 ml NMP
0.500 gm paraformaldehyde (95%) 15.8 mmoles
1.5:1H$_2$:CO charged to 4500 psig at 27° C.
which was heated at 250° C. for two hours. Analysis of the product gave the following results:

| Product distribution | % yield |
|---|---|
| CH$_3$OH = 7.80 mmoles | 49.4 |
| CH$_3$CHO = .79 mmoles | 5.0 |
| C$_2$H$_5$OH = 2.88 mmoles | 18.2 |

This procedure was repeated except no HBr was present. Analysis of the product showed that only methanol was produced.

EXAMPLE 5

The procedure of EXAMPLE 4 was repeated with the following charge with the indicated product yield:
0.0248 gm [RuCl$_2$(CO$_3$]$_2$
1 ml HBr/NMP solution containing 0.1 mmole HBr per ml
4 ml NMP
0.500 gm paraformaldehyde (95%) 15.8 mmoles
1.5:1 H$_2$:CO charged to 4500 psig at 27° C.

| Product distribution | % yield |
|---|---|
| CH$_3$OH = 9.82 mmoles | 62.2 |
| CH$_3$CHO = .46 mmoles | 2.9 |
| C$_2$H$_5$OH = 3.82 mmoles | 24.2 |

EXAMPLE 6

The procedure of EXAMPLE 4 was repeated with the following charge with the indicated product yield:
0.0252 gm [RuCl$_2$(CO)$_3$]$_2$
5 ml NMP
0.500 gm paraformaldehyde (95%) 15.8 mmoles
1.5:1 H$_2$:CO charged to 4500 psig at 27° C.

| Product distribution | % yield |
|---|---|
| CH$_3$OH = 7.33 mmoles | 46.4 |
| CH$_3$CHO = .55 mmole | 3.5 |
| C$_2$H$_5$OH = 3.46 mmoles | 21.9 |

EXAMPLE 7

The procedure of EXAMPLE 4 was repeated with the following charge with indicated product yield:
0.043 gm of a lithium bromocarbonyl ruthenate
0.5 gm paraformaldehyde
5 ml NMP
1.5:1 H$_2$:CO charged to 4500 psig at 26° C.
2 hrs. at 120° C.
  yield methanol=5%
  yield acetaldehyde=9%
  yield ethanol=0.1%

EXAMPLE 8

The procedure of EXAMPLE 4 was repeated with the following charge:
0.025 gm [RuCl$_2$(CO)$_3$]$_2$
0.5 gm paraformaldehyde
5 ml 1,1,3,3-tetramethylurea
1.5:1 H$_2$:CO charged to 4500 psig at 17° C.
2 hrs. at 150° C.

Substantial amounts of acetaldehyde and ethanol were formed. Principal by-product was methanol.

EXAMPLE 9

The procedure of EXAMPLE 4 was repeated with the following charge with indicated product yield:
0.025 gm [RuCl$_2$(CO)$_3$]$_2$
0.5 gm paraformaldehyde
5 ml gamma-butyrolactone
1.5:1 H$_2$:CO charged to 4500 psig at 19.5° C.
2 hrs. at 130° C.
    yield methanol=34%
    yield ethanol=5%

EXAMPLE 10

The procedure of EXAMPLE 4 was repeated with the following charge with indicated product yield:
0.020 gm Ru$_3$(CO)$_{12}$—as the source of ruthenium
0.012 gm (C$_2$H$_5$)$_2$TiCl$_2$—as the source of halide
0.5 gm paraformaldehyde
10 ml NMP
1.5:1 H$_2$:CO charged to 4500 psig at 30° C.
2 hrs. at 130° C.
    yield methanol=12.7%
    yield acetaldehyde=12.1%

EXAMPLE 11

The procedure of EXAMPLE 4 was repeated with the following charge with indicated product yield:
0.020 gm Ru$_3$(CO)$_{12}$—as the source of ruthenium
0.016 gm CsCl—as the source of halide
0.5 gm paraformaldehyde
5 ml NMP
1.5:1 H$_2$:CO charged to 4500 psig
2 hrs. at 130° C.
    yield methanol=11%
    yield acetaldehyde=0.8%

In the foregoing examples, the products were identified by gas-liquid chromatography and/or mass spectrum analysis.

What is claimed is:

1. A process which comprises reacting formaldehyde, carbon monoxide and hydrogen at a temperature of from about 75° to about 250° C. and superatmospheric pressure to form acetaldehyde in a first reaction stage and then ethanol in a second reaction stage, wherein a catalyst system initially comprised of a source of ruthenium and a source of halide is present at least during said first reaction stage.

2. A process according to claim 1 wherein said ruthenium is present during said second reaction stage.

3. A process according to claim 1 wherein a hydrogenation catalyst is present during said second stage reaction.

4. A process according to claim 3 wherein said ruthenium is removed from the first reaction stage product prior to said second stage reaction.

5. A process according to claim 3 wherein said hydrogenation catalyst comprises palladium.

6. A process according to claim 1 wherein said first and second stage reactions are conducted at a temperature of from about 100° to about 175° C.

7. A process for producing acetaldehyde and/or ethanol which comprises reacting formaldehyde, carbon monoxide and hydrogen at a temperature of from about 75° to about 250° C. and superatmospheric pressure in the presence of a catalyst system initially comprised of a source of ruthenium and a source of halide and recovering acetaldehyde and/or ethanol from said reaction.

8. A process according to claim 7 wherein said temperature is in the range of from about 100° to about 175° C. and said pressure is in the range of from about 150 to about 600 atmospheres.

9. A process according to claim 1 wherein the molar ratio of hydrogen to carbon monoxide is from about 1/10 to about 10/1.

10. A process according to claim 7 wherein the reaction is carried out in the presence of a solvent comprising an aprotic organic amide.

11. A process according to claim 10 wherein the solvent comprises an N-lower alkyl pyrrolidin-2-one.

12. A process according to claim 10 wherein the solvent comprises an N,N-di(lower alkyl)acetamide.

13. A process according to claim 10 wherein the solvent comprises N-methyl pyrrolidin-2-one.

14. A process according to claim 10 wherein the solvent comprises N,N-diethyl acetamide.

15. A process according to claim 10 wherein the solvent comprises N,N-diethyl propionamide.

16. A process according to claim 7 wherein the reaction is carried out in the presence of a solvent comprising tetrahydrofuran.

17. A process according to claim 7 wherein the reaction is carried out in the presence of a solvent comprising gamma butyrolactone.

18. A process according to claim 7 wherein the reaction is carried out in the presence of a solvent comprising 1,1,3,3-tetramethylurea.

19. A process for producing ethanol and/or acetaldehyde by reacting formaldehyde, carbon monoxide and hydrogen in a solvent comprising an aprotic organic amide at a temperature of from about 75° to about 250° C. and superatmospheric pressure in the presence of a catalyst system initially comprised of a source of ruthenium and a source of halide and recovering ethanol and/or acetaldehyde.

20. A process according to claim 19 wherein the solvent comprises an N-lower alkyl pyrrolidin-2-one.

21. A process according to claim 19 wherein the solvent comprises N-methyl pyrrolidin-2-one.

22. A process according to claim 19 wherein the temperature is from about 100° to about 175° C. and the pressure is from about 150 to about 600 atmospheres.

* * * * *